(12) United States Patent
Hezemans et al.

(10) Patent No.: US 8,977,343 B2
(45) Date of Patent: Mar. 10, 2015

(54) OPTICAL PROBE HAVING A POSITION MEASURING SYSTEM

(75) Inventors: Cornelius A. Hezemans, Nuenen (NL); Bernardus H. W. Hendriks, Eindhoven (NL); Waltherus C. J. Bierhoff, Eindhoven (NL); Augustinus L. Braun, Heeze (NL); Adrien E. Desjardins, Waterloo (CA)

(73) Assignee: Koninklijke Philips N.V., Eindhoven (NL)

( * ) Notice: Subject to any disclaimer, the term of this patent is extended or adjusted under 35 U.S.C. 154(b) by 279 days.

(21) Appl. No.: 13/125,812

(22) PCT Filed: Oct. 21, 2009

(86) PCT No.: PCT/IB2009/054644
§ 371 (c)(1),
(2), (4) Date: Apr. 25, 2011

(87) PCT Pub. No.: WO2010/049854
PCT Pub. Date: May 6, 2010

(65) Prior Publication Data
US 2011/0201922 A1     Aug. 18, 2011

(30) Foreign Application Priority Data
Oct. 28, 2008   (EP) .................................... 08167689

(51) Int. Cl.
*A61B 18/14*   (2006.01)
*G01B 7/00*    (2006.01)
*A61B 1/00*    (2006.01)
*A61B 5/00*    (2006.01)
(Continued)

(52) U.S. Cl.
CPC ......... *A61B 1/00188* (2013.01); *A61B 1/00096* (2013.01); *A61B 1/00163* (2013.01); *A61B 1/00165* (2013.01); *A61B 5/0062* (2013.01); *A61B 5/0084* (2013.01); *A61B 5/061* (2013.01); *A61B 5/062* (2013.01); *A61B 5/065* (2013.01); *A61B 19/5212* (2013.01); *A61B 2019/2253* (2013.01); *A61B 2019/5251* (2013.01)
USPC ............................................... 600/424; 850/1

(58) Field of Classification Search
USPC ......................................................... 600/424
See application file for complete search history.

(56) References Cited

U.S. PATENT DOCUMENTS

| | | | |
|---|---|---|---|
| 6,220,084 B1 * | 4/2001 | Chen et al. ..................... | 73/105 |
| 6,845,190 B1 | 1/2005 | Smithwick et al. | |
| 7,123,790 B2 * | 10/2006 | Rosman et al. ................. | 385/25 |

(Continued)

FOREIGN PATENT DOCUMENTS

EP          1901107 A1    3/2008

*Primary Examiner* — Tse Chen
*Assistant Examiner* — Patricia Park (57) ABSTRACT

An optical probe and an optical imaging system include an optical guide, and an actuator having driving coils and a magnet. By supplying a driving current through the driving a magnetic flux is generated which causes a displacement of the distal end of the optical guide. A position measuring device includes a position measuring coil used for monitoring the position of the optical guide, where displacement of the guide distal end causes change in the relative positions of the measuring and driving coils. A power supply supplies a high frequency AC current through the driving coils which causes, an induced voltage in the position measuring coil and thus generates a magnetic coupling between the measuring and driving coils. This induced voltage change is indicative for the position of the distal end.

15 Claims, 5 Drawing Sheets

(51) Int. Cl.
*A61B 5/06* (2006.01)
*A61B 19/00* (2006.01)

(56) References Cited

U.S. PATENT DOCUMENTS

| 7,608,842 | B2 * | 10/2009 | Johnston | 250/492.1 |
| 8,060,184 | B2 * | 11/2011 | Hastings et al. | 600/424 |
| 8,212,884 | B2 * | 7/2012 | Seibel et al. | 348/220.1 |
| 2002/0019644 | A1 * | 2/2002 | Hastings et al. | 606/159 |
| 2002/0177237 | A1 * | 11/2002 | Shvets et al. | 436/180 |
| 2003/0183761 | A1 * | 10/2003 | Hantschel et al. | 250/306 |
| 2003/0206321 | A1 | 11/2003 | Gelikonov et al. | |
| 2004/0075428 | A1 * | 4/2004 | Proksch et al. | 324/207.18 |
| 2006/0013528 | A1 | 1/2006 | Rosman et al. | |
| 2008/0101677 | A1 | 5/2008 | Maschke et al. | |

* cited by examiner

OPTICAL PROBE HAVING A POSITION MEASURING SYSTEM

FIELD OF THE INVENTION

The present invention relates to an optical probe suitable for miniature applications, e.g. in-vivo medical inspections and procedures or in industrial inspections, for instance inspection of food or small devices. The invention also relates to a corresponding imaging system and a method for imaging with such an imaging system.

BACKGROUND OF THE INVENTION

Figure 1:
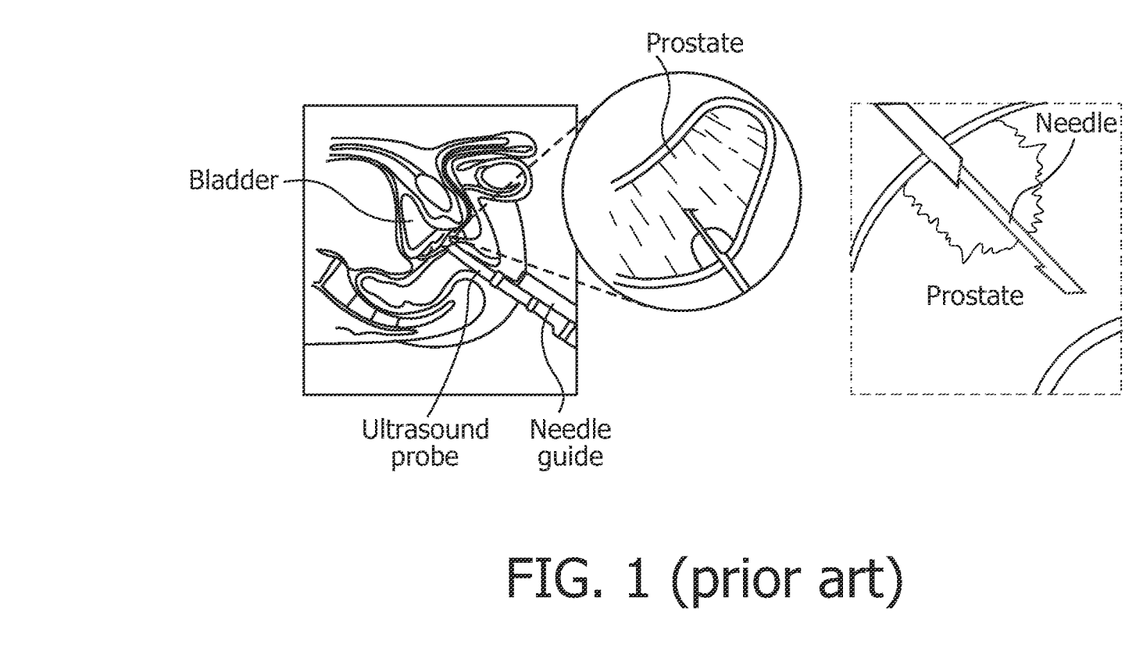
FIG. 1 depicts graphically the process of taking a biopsy via the rectum under ultrasound guidance.

For correct diagnosis of various cancer diseases biopsies are taken. This can either be via a lumen of an endoscope or via needle biopsies. An example of a needle biopsy is shown in FIG. 1, where a biopsy is taken from the prostate via the rectum. In order to find the correct position to take the biopsy, various imaging modalities are used such as X-ray, MRI and ultrasound. In case of prostate cancer in most cases the biopsy is guided by ultrasound. Although helpful, these methods of guidance are far from optimal. The resolution is limited and, furthermore, these imaging modalities can in most cases not discriminate between benign and malignant tissue. As a result one does not know for certain that from the correct part of the tissue a biopsy is taken. The biopsies are almost blind biopsies and even if after inspection of the tissue no cancer cells are detected, it is not known for certain that one did not simply miss the right spot to take the biopsy. Accordingly, since these biopsies are performed without direct feedback this procedure is prone to errors.

BRIEF DESCRIPTION OF THE INVENTION

The object of the present invention is to provide a fiber-optic system that allows a direct inspection during the biopsy procedure.

According to one aspect the present invention relates to an optical probe, comprising:
  an optical guide having a proximal end and a distal end,
  an actuation means comprising at least one driving coil and
    a magnet either of which being attached to the optical guide, whereby supplying a driving current through the at least one driving coil a magnetic flux is generated which interacts with the magnet and forms a driving force acting on the optical guide causing a displacement of the distal end of the optical guide,
  a position measuring system comprising:
    a position measuring coil for monitoring the position of the optical guide, the internal arrangement of the position measuring coil and the at least one driving coil being such that said displacement of the distal end of the optical guide causes a change in the internal arrangement,
    a power supply for supplying an additional sensing current through the at least one driving coil, the additional sensing current causing an induced voltage in the position measuring coil and thus generates a magnetic coupling between the position measuring coil and the at least one driving coil, and
    a position measuring means for measuring the displacement of the distal end of the optical guide by means of measuring the induced voltage resulting in when said internal arrangement changes, the induced voltage being indicative for the position of the distal end.

In that way, by measuring the induced voltage change resulting in when said internal arrangement changes a direct feedback signal is provided indicating the precise position of the lens system. Such an optical probe is particularly suited for miniature applications e.g. for in-vivo medical application. It should further be mentioned that the optical probe according to the present invention is particularly suited for relative simple and large-scale manufacturing because of the lens system being displaceably mounted on the end portion optical guide. From a practical point of view, this may reduce the needed precision during manufacturing which, in turn, may lower the unit-price per probe. This is especially important because an endoscope, a catheter or needle with the optical probe embedded will normally be disposed after a single use due to sanitary requirements.

In one embodiment, the sensing current is a high frequency alternating current (AC), the frequency of the AC being selected such that its contribution to the displacement of the optical guide is minimized.

In one embodiment, the position measuring coil is mounted around the optical guide such that the longitudinal axis of the position measuring coil is substantially parallel to the longitudinal axis of the optical guide.

In one embodiment, the at least one driving coil comprises X-driving coils are arranged opposite to each other along x-axis with the optical guide there between such that the longitudinal axis of the driving coils is perpendicular to the longitudinal axis of the optical guide, the driving current supplied through the X-driving coils causing displacement of the end portion of the optical guide along the x-axis.

In one embodiment, the at least one driving coil comprise Z-driving coils are arranged opposite to each other along z-axis with the optical guide there between such that the longitudinal axis of the driving coils is perpendicular to the longitudinal axis of the optical guide, the driving current supplied through the Z-driving coils causing displacement of the end portion of the optical guide along the z-axis perpendicular to the x-axis.

In one embodiment, said sensing current is said high frequency AC, the frequency of the sensing current supplied through the X-coils being different from the high frequency AC current through the Z-coils.

Accordingly, by using one specific high frequency AC for the sensing current in the X-driving coils and a different high frequency AC for the sensing current through the Z-driving coils, the signal induced in the measuring coils contains information on the X-position and on the Z-position at the same time. By appropriately filtering the measuring signal, both the X-position and the Z-position can be determined.

In one embodiment, the frequency of the high frequency AC is in the range of 100 kHz-1 MHz.

In one embodiment, the optical probe further comprises a lens system is rigidly coupled to the distal end of the optical guide.

In one embodiment, the optical probe further comprises a housing with a cavity for the optical guide, the housing having at its distal end a transparent window.

In one embodiment, the at least one driving coil is mounted to the housing and the position measuring coil is mounted to the optical guide.

In one embodiment, the at least one driving coil is mounted to the optical guide and the position measuring coil is mounted to the housing.

According to another aspect, the present invention relates to an optical imaging system, comprising
  said optical probe, a radiation source optically coupled to the optical probe, the probe being arranged for guiding radiation emitted from the radiation source to a region of interest, and an imaging detector optically coupled to the optical probe, the detector being arranged for imaging using reflected radiation from the region of interest.

In one embodiment, the frequency of the sensing current is in the range of 100 kHz-1 MHz.

In one embodiment, the frequency of the driving current is up to 1 kHz.

According to still another aspect, the present invention relates to a method for optical imaging, the method comprising:

providing said optical probe, providing a radiation source which is optically coupled to the optical probe, the probe being arranged for guiding radiation emitted from the radiation source to a region of interest, and performing an imaging process with an imaging detector optically coupled to the optical probe, the detector being arranged for imaging using reflected radiation from the region of interest.

The aspects of the present invention may each be combined with any of the other aspects. These and other aspects of the invention will be apparent from and elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figure 2:
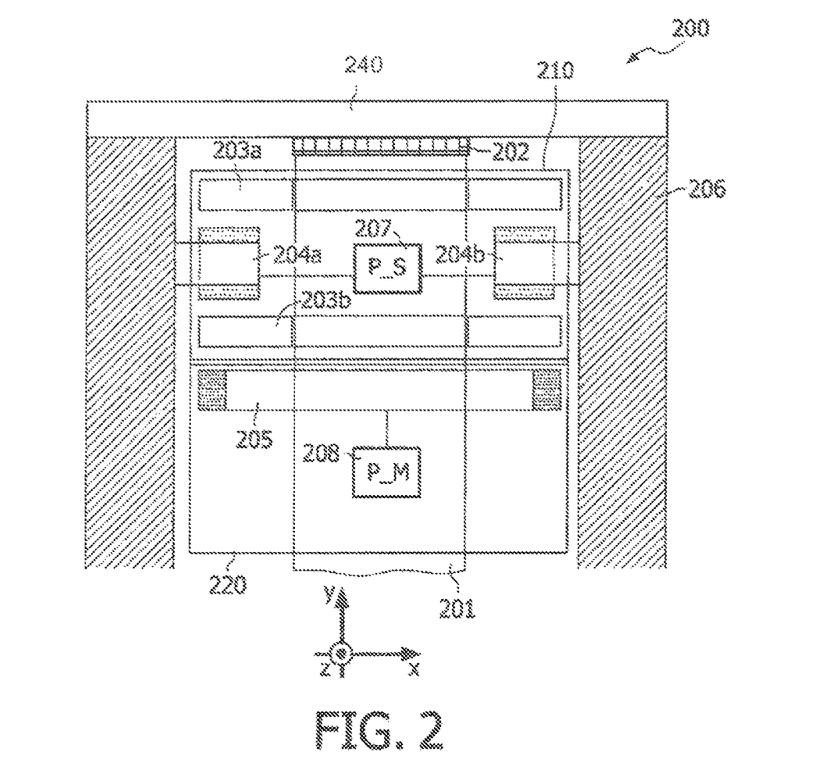
FIG. 2 is a schematic drawing of an optical probe according to the present invention, FIG. 3a,b depicts graphically the scenario where the optical guide is in a rest position and where the optical guide is displaced to the right along the x-axis.

FIG. 2 shows an optical probe 200 according to the present invention, comprising an optical guide 201, an actuating means 210 and a position measuring system 220.

Typically, the optical guide 201 is made of a flexible material so as to facilitate inspection on not easy accessible positions, e.g. in-vivo medical inspection and/or sample taking. Various solutions for displacement of an optical guide at an end of a probe are discussed in US2001/0055462, which is hereby incorporated by reference in its entirety.

In the context of the present invention it is to be understood that the term "optical guide" may include, and is not limited to, optical fibres (multi-mode and single-mode), thin film optical paths, photonic crystal fibres, photonic bandgab fibres (PBG), polarization maintaining fibres, and the like. The optical probe may also comprise more than one fibre i.e. a plurality of fibres or a fibre bundle.

In one embodiment, the optical probe 200 further comprises a lens system 202 rigidly coupled to the distal end of the optical guide 201. The lens system 202 may e.g. be mounted directly to the optical guide 201 in order to enhance the field of view, or it may be mounted to the housing. In one embodiment, the lens system 202 is a single lens system because this simplifies manufacturing even more and makes the miniature requirements easier to fulfill. Possibly, the lens system 202 may comprise an aspherical lens i.e. the lens is not a spherical lens which thereby facilitate a relative high numerical aperture and accordingly a quite compact lens system is obtained. In another embodiment, the lens system 202 may comprise a fluid lens with a changeable numerical aperture. For the example, the lens system 202 may comprise a liquid lens with an oil-water two-phase system as described in U.S. Pat. No. 7,126,903, hereby incorporated by reference. Thereby the numerical aperture can be tuned so that focal depth changes are facilitated. The lens system 202 may also have more than one lens and also may contain diffractive elements or mirror elements. The coupling between the lens system 202 and the optical guide 201 may be mechanical i.e. there may be an intermediate mount (not shown here) keeping the position of the lens system 202 and the optical exit of the optical guide 201 is an fixed position relative to each other.

The actuation means 210 comprises at least one driving coil 204a,b and one or more magnets 203a,b, where either the one or more magnets 203a,b is attached to the optical guide 201 while the at least one driving coil 204a,b is in a rigid position or vice verse, the at least one driving coil 204a,b is attached to the optical guide 201 while the one or more magnets 203a,b are in a rigid position.

The embodiment here shows two X-driving coils arranged opposite to each other along x-axis with the optical guide there between such that the longitudinal axis of the driving coils (the x-axis) is perpendicular to the longitudinal axis of the optical guide 201 (y-axis). The magnet(s) may have a cylindrical shape such that the central axis of the magnet(s) may be mounted transversally to the optical guide 201 such that the longitudinal axis of the magnet(s) (y-axis) is parallel to the longitudinal axis of the optical guide 201 (y-axis). By supplying a driving current through the driving coils 204a,b a magnetic flux is generated which interacts with the magnet which form a driving force acting on the optical guide causing a displacement of the distal end of the optical guide.

The position measuring system 220 comprises a position measuring coil 205 for monitoring the position of the distal end of the optical guide 201, a power supply (P_S) 207 and a position measuring means (P_M) 208.

The internal arrangement between the position measuring coil 205 and the driving coils 204a,b is selected such that the displacement of the distal end portion of the optical guide causes a change in the internal arrangement.

In one embodiment, this is realized by mounting the position measuring coil 205 rigidly around the optical guide 201 such that the longitudinal axis (the y-axis, see the coordinate system) of the position measuring coil 205 is substantially parallel to the longitudinal axis (y-axis) of the optical guide 201, and mounting the driving coils 204a,b rigidly such that the displacement of the optical guide 201 does not affect the position of the driving coils. This may e.g. be done by mounting the driving coils 204a,b to a housing 206 that has a cavity where the optical guide 201 can be embedded. In that way, the displacement of the optical guide causes a displacement of the position measuring coil 205 relative to the driving coils 204a,b. In another embodiment, the internal displacement may also be achieve by mounting the driving coils 204a,b to the optical guide 101 and the position measuring coil to the housing 206 (not shown here). In this case the magnets 204 must be mounted to the housing 206.

The housing comprises window 240 that may be a plane section of an optical transport glass or polymer. The window 240 is preferably non-focussing i.e. it has no optical power, but it is contemplated that the window 240 may for some applications have some focussing effect. This is however not usually the case because it may influence the performance of the lens system 202. It is nevertheless contemplated that the exit window 240 in some cases may be a field flattener lens to make the image plain flat and not curved and this requires a small amount of optical power.

The driving coils 204a,b may include one or more X-driving coils. In the embodiment in FIG. 2, there are two X-driving coils, arranged along the x-axis opposite to each other with the optical guide there between such that the longitudinal axis of the driving coils (x-axis) is perpendicular to the longitudinal axis (y-axis) of the optical guide 201. Thus, the driving current supplied through the X-driving coils causes a displacement of the distal end of the optical guide 201 along the x-axis (and thus the lens system 202), i.e. to move left and right. The number of X-driving coils could of course include more than two driving coils, where the optical guide could situated somewhere between these X-driving coils.

The driving coils preferably comprise further one or more Z-driving coils (not shown here) to allow displacement of the distal end of the optical guide 201 along the z-axis, i.e. in and out of the plane. As an example, the Z-driving coils could be two arranged opposite to each other with the with the optical guide there between (e.g. in the center) such that the longitudinal axis of the driving coils is perpendicular to the longitudinal axis of the optical guide so that the driving current supplied through the two Z-driving coils causes displacement of the distal end of the optical guide (and thus the lens system 202) along the z-axis perpendicular (in/out of the plane) to the x-axis.

Accordingly, the interplay between the X and the Z-driving enables optical scanning of a region of interest outside the said window.

Figures 3A, 3B:
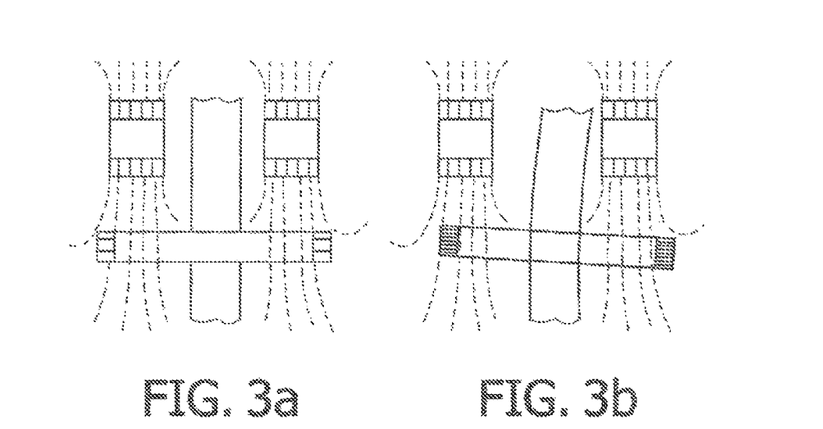

The power supply (P_S) 207 supplies among other things an additional sensing current through the driving coils, where the frequency of the sensing current is selected such that its contribution to the displacement of the optical guide 201 is minimized. This additional sensing current causes an induced voltage in the position measuring coil 205 and thus generates a magnetic coupling between the position measuring coil and the driving coils. This will be discussed in more details in FIG. 3. In one embodiment, the sensing current is a high frequency alternating current (AC). The frequency may be within the range of 100 kHz-1 MHz. This is however not limited to this range. The frequency could just as well be somewhat above this range or below this range.

The position measuring means (P_M) 208 is adapted for measuring the displacement of the distal end of the optical guide 201 by means of measuring the induced voltage resulting in when the internal arrangement changes, the induced voltage being indicative for the position of the distal end.

Referring to said X and Z-coils, in one embodiment the high frequency AC driving through the X-coils is different from the high frequency AC current through the Z-coils. By applying different high frequency AC for the sensing current in the X-driving coils and a different high frequency AC for the sensing current through the Z-driving coils, the signal induced in the measuring coils contains information on the X-position and on the Z-position at the same time. By appropriately filtering the measuring signal, both the X-position and the Z-position can be determined, i.e. the coordinate (x,z).

As already mentioned, the magnets 203a,b and the driving coils 204a,b deliver the drive force. The current in the X-coils exists of two parts, said driving current (Idrive) and said high frequency current, here below referred as a sensing current, or Isense. Thus, the current through said X-coils is Idrive_x+Isense_x, and in said Z-coils, Idrive_z+Isense_z. In one embodiment, Isense are selected such that Isense_x and Isense_z are averaged 0, so that no drift in the off-set can occur, and they are characterized in that the frequencies of the sensing currents applied to the coils for driving the motor are sufficiently high that their contribution to the displacement of the fiber is negligible. The contribution to the displacement should be preferably less than 5%, even more preferred less than 1%, while in the ideal situation less than 0.1%.

Here below, for simplicity only the x-dimension is mentioned, but it also holds for the z-dimension. The direction of Isense_x in the one or more X-driving coils is so that the voltage in the sense coil, induced by this Isense_x, is zero when the magnetic coupling between the X-driving coils and the sense coil is the same.

FIG. 3a,b depicts graphically the scenario where the optical guide is in a rest position (FIG. 3a) and where the optical guide is displaced to the right along the x-axis. In this example, it is assumed that the position measuring coil 205 is mounted to the optical guide 201 and that the driving coils are mounted to the housing 206.

In FIG. 3a, the magnetic coupling between the X-driving coils and the position measuring coil 205 is such that the magnetic flux from the two X-driving coils through the position measuring coil 205 is the same and the induced voltage is zero.

In FIG. 3b, the displacement of the distal end portion of the optical guide 201 causes a displacement of the position measuring coil 205 whereas the two X-driving coils 204a,b remain fixed in their original position, and thus a change in the internal arrangement between the position measuring coil 205 and the two X-driving coils 204a,b. This change causes a change in the magnetic coupling meaning that the magnetic flux (field lines) that enters the position measuring coil 205 at the left side (as depicted here, three lines enter the left side) is less than that on the right side. Accordingly, this change in the "balance" between the magnetic field lines causes an induced voltage, which is indicative to the displacement. Put in other words, the coupling between the position measuring coil 205 and the driving coil 204b is higher than the coupling between the position measuring coil 205 and the driving coil 204a.

This causes the amplitude of the induced voltage in the position measuring coil 205 to change with this displacement while the phase, compared to the phase of the Isense_x, changes 180 degrees with the direction, + or −, of the displacement. As an example, a positive induced voltage may indicate that the optical guide 201 is moving to the left on the x-axis, and a negative voltage may indicate that it is moving to the right on the x-axis. Also, the precise position on the x-axis may easily be derived via calibration where various induced voltage and the corresponding locations (measured by the appropriate measuring methods) are determined. Typically, the amplitude of the induced voltage in the position measuring coil 205 changes more or less linearly with this displacement.

As discussed previously, an extra high frequency AC Isense_x may be applied through the driving coils 204a,b as a sensing current. In case of additional Z-coils (not shown here), it is preferred to use a Isense_z current which is different from Isense_x current, because in that way and by using the appropriate filtering technique, it is possible to distinguish between the displacement along the x-axis and the z-axis.

The voltage of the sense coil, in which these amplitude and phase changes take place, has as mentioned before preferably a high frequency. These changes in the voltage with this frequency can be demodulated by the well known method of synchronous detection by e.g. means of multiplying the sense coil output voltage with a sinusoidal voltage with the same frequency and a well chosen phase and filtering the multiplier output with a low pass filter. This synchronous detection makes it possible to measure simultaneously the 2 dimensions x and z by choosing the frequency of Isense_x=Fx different from the frequency of Isense_z=Fz, and multiplying the sense coil output with voltages with frequencies Fx and Fz. The low pass filtered output of the multiplication with the voltage with frequency Fx gives the output depending on the x displacement, while the other output depends on the z displacement.

10× Scaling:

To verify the results of the precise position measuring, 10× larger model was built up to test the principle. The results below are the measurements showing that it works and what accuracy we obtained.

Figure 4:
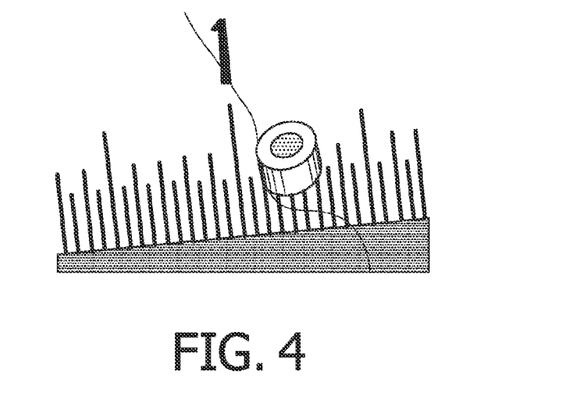
FIG. 4 shows an position measuring coil.
Figure 5:
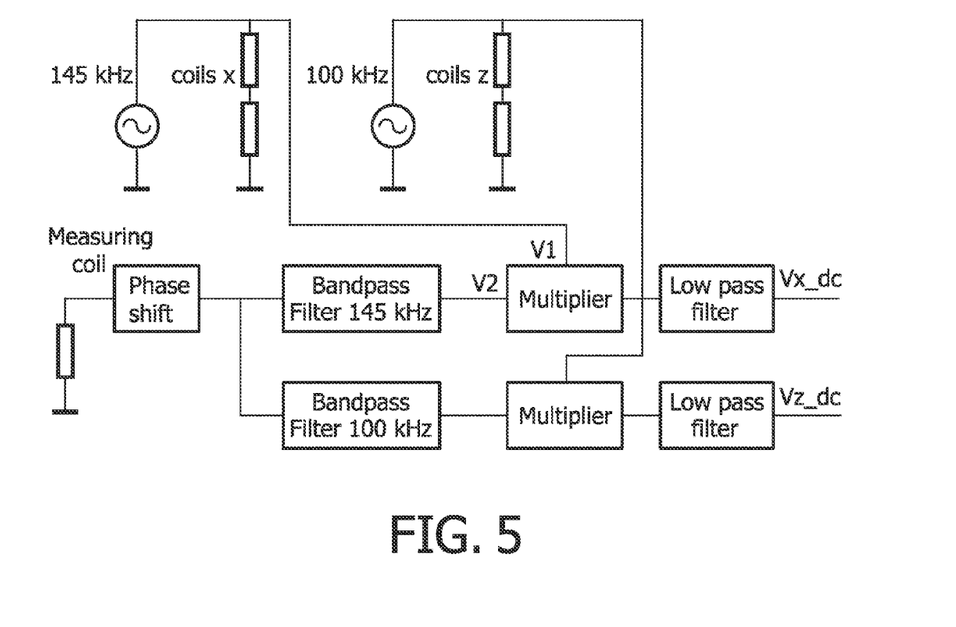
FIG. 5 shows an example of a block diagram showing a measuring setup.

FIG. 5 shows an example of a block diagram of the measurement setup, where a position measuring coils as shown in FIG. 4 with an outer diameter of 32 mm was used. The housing 206 was made of RVS cylinder.

Vx_dc and Vz_dc are measured as function of Δx and Δz with Vx_dc and Vz_dc in mV. In table 1 the measured voltages for different positions of the optical guide (in this case an optical fiber) i.e. for different positions of the position measuring coil 205 with respect to the driving coils 204a,b. To determine the accuracy with which the position can be measured the data must be inverted.

TABLE I

| Δz in μm ↓ \ Δx→ in μm | -1000 | -750 | -500 | -250 | 0 | 250 | 500 | 750 | 1000 |
|---|---|---|---|---|---|---|---|---|---|
| 1000 | | | | | 1 / -95 | | | | |
| 750 | | -73 / -76 | | | 1 / -71 | | | 75 / -67 | |
| 500 | | | -49 / -51 | | 1 / -47 | | 50 / -44 | | |
| 250 | | | | -25 / -25 | 0 / -23 | 25 / -22 | | | |
| 0 | -99 / -7 | -75 / -5 | -50 / -3 | -25 / -1 | 0 / 0 | 24 / 1 | 50 / 3 | 75 / 4 | 100 / 5 |
| -250 | | | | -25 / 22 | -1 / 23 | 24 / 25 | | | |
| -500 | | | -50 / 43 | | -1 / 47 | | 49 / 50 | | |
| -750 | | -75 / 65 | | | -1 / 71 | | | 73 / 75 | |
| -1000 | | | | | 1 / 94 | | | | |

A matrix A is defined by $$\begin{pmatrix} Vx\_dc \\ Vz\_dc \end{pmatrix} = A * \begin{pmatrix} \Delta x \\ \Delta z \end{pmatrix}$$

and is calculated from Δz with Δx=0 and from Δx with Δz=0. The inverse of this matrix $$\begin{pmatrix} \Delta x \\ \Delta z \end{pmatrix} = A^{-1} * \begin{pmatrix} Vx\_dc \\ Vz\_dc \end{pmatrix}$$

transforms the measured voltages into a table in Δx and Δz data. The difference between these calculated values and the given Δx and Δz is the error and are shown in Table 2, which shows the accuracy in position measurement obtained with the measurement coil. This table shows that the accuracy for displacements up to 1.4 mm are smaller than 18 microns. The errors are shown in vector form:

$$\begin{pmatrix} \Delta x \\ \Delta z \end{pmatrix}$$

and are in μm.

TABLE II

| Δz in μm ↓ \ Δx→ In μm | -1000 | -750 | -500 | -250 | 0 | 250 | 500 | 750 | 1000 |
|---|---|---|---|---|---|---|---|---|---|
| 1000 | | | | | 0 / 0 | | | | |
| 750 | | | 5 / 3 | | 3 / -2 | | 0 / 3 | | |
| 500 | | | | 0 / 5 | 5 / -5 | 0 / -5 | | | |
| 250 | | | | 5 / -3 | -2 / -8 | 0 / -3 | | | |
| 0 | -1 / 11 | -8 / 5 | -5 / 0 | -2 / -5 | 0 / 0 | -8 / 5 | 5 / 0 | 8 / 6 | 10 / 11 |
| -250 | | | | 0 / -3 | -8 / 7 | -5 / 2 | | | |
| -500 | | | | 0 / -16 | -5 / 5 | 0 / 5 | | | |
| -750 | | | 0 / 18 | | -3 / 2 | | -5 / 8 | | |
| -1000 | | | | | 0 / 11 | | | | |

Figure 6:
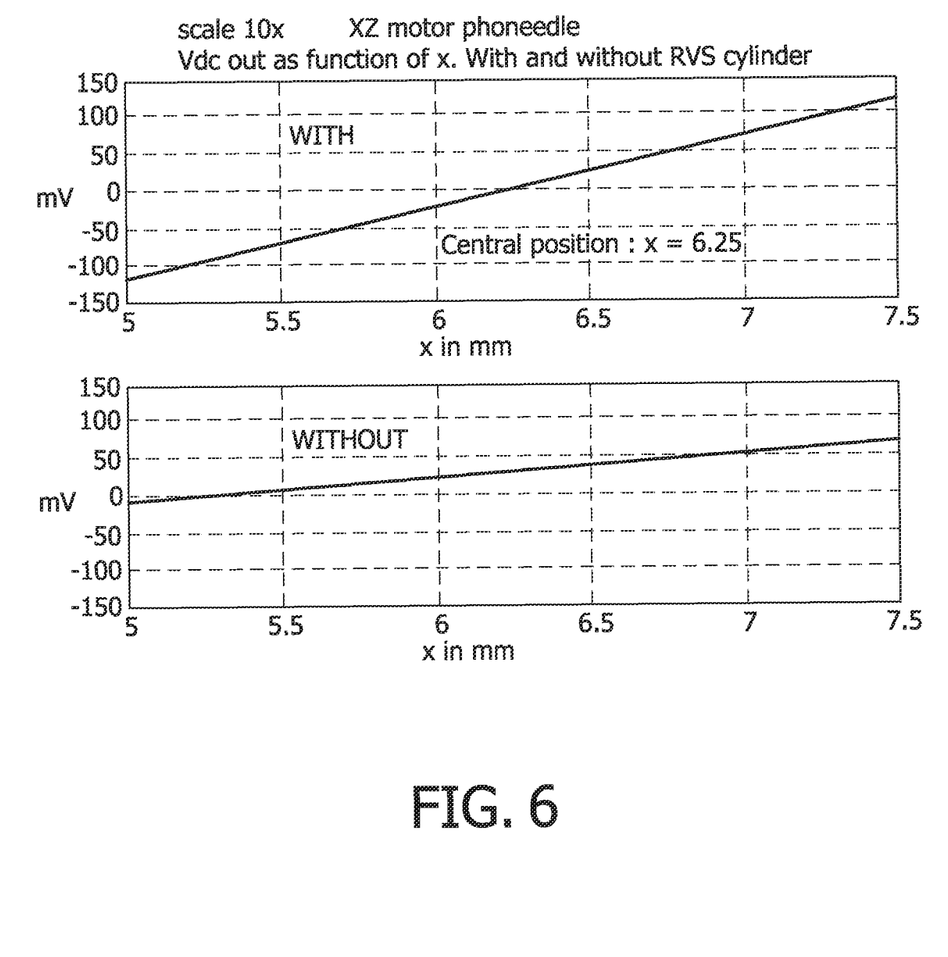
FIG. 6 shows two diagrams of measured induced voltage in the position measurement coil as a function of the distance from the driving coils with and without a housing (RVS cylinder)

In the previous example there was a metal (RVS) cylinder present as will be the case in most needle like scanners. However, in some cases the housing of the needle (for instance MRI applications) must be non-metal. To investigate the influence of the metal cylinder a comparison is made. In FIG. 6 the results with and without RVS cylinder are shown for Vx_dc. The signal with cylinder is higher and more symmetrical, hence with cylinder is a more preferred solution.

Current in x-coils=26 mA eff, frequency=145 kHz
N of x, z coils, each coil=160 turns, N of measuring coil=250 turns.
Voltage across x-coils=7.9 Vp
Amplification bandpass filter=8.3 at 145 kHz.
Multiplier: v1*v2/10
Transfer of electronics by filter+multiplierc+1p filter: 125 mVp on measuring coil gives 334 mVdc
Measurement with RVS cylinder:
Phase shift=0.
ΔVdc=220 mV over Δx=2.2 mm
Calculation of mVp on measuring coil per N^2 and per Amp_eff over Δx=2.2 mm: 220/334*125/160/250/0.026=79e-3 mVp/N^2/Aeff.
1× Scale:
When all dimensions change with a factor α, the voltage of the measuring coil is expected to change also with α.
Comparison of the measurements 10× scale and 1× scale model with RVS cylinder are following:
Current in x-coils=77 mA eff, frequency=145 kHz.
N of x, z coils, each coil=90 turns.
N of measuring coil=129 turns.
Measurement: at Δx=0.22 mm the ΔVp on the measuring coil=1.75 mVp This gives in mVp per N^2 and per Amp_eff: 1.75/129/90/0.077=2e-3: 4 times less than expected from the 10× scale model, =79e-3.

The low output of the measuring coil makes it more difficult to discriminate between the wanted x, z dependent measuring voltage and the unwanted cross-talk from the coils-x and coils-z wires into the measuring coil wires.

Although the scaling law seems not to hold, the results still show that with smaller dimensions the invention works well as a position sensor.

Figure 7:
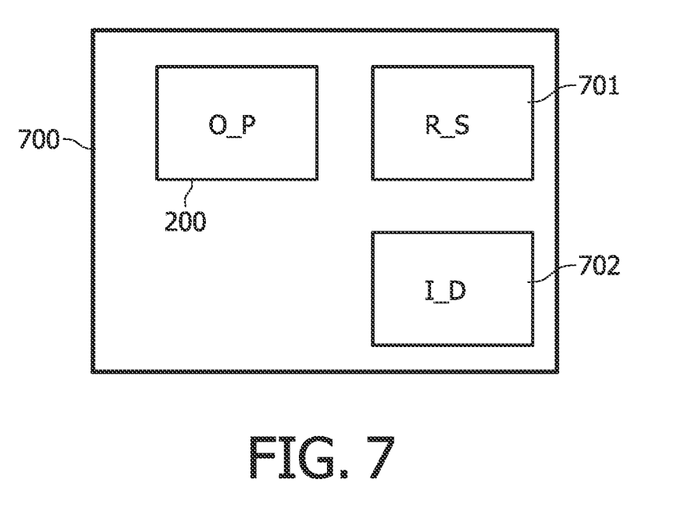
FIG. 7 shows an optical imaging system according to the present invention.

FIG. 7 shows an optical imaging system 700 according to the present invention comprising said optical probe 200 (see FIG. 2), a radiation source (R_S) 701 and an imaging detector (I_D) 702. The radiation source (R_S) 701 is optically coupled to the optical probe 200, which is arranged for guiding radiation emitted from the radiation source to a region of interest outside said window 240 (see FIG. 2). The imaging detector (I_D) 702 is arranged for imaging using reflected radiation from the region of interest in the sample (not shown). The imaging detector (I_D) 702 may also comprise a user interface (UI) so accessing results and/or controlling the imaging process.

In the context of the present invention it is to be understood that the term "radiation source" may comprise any suitable kind of radiation source including, and not limited to, lasers (of any wavelength and any mode of operation i.e. continuous or pulsed of any period incl. femto seconds laser), LEDs, gas-discharge lamps, any kind of luminescence, etc.

Figure 8:
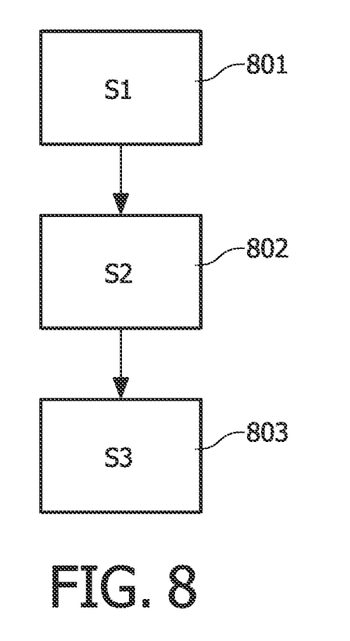
FIG. 8 shows a flowchart of a method according to the present invention for optical imaging.

FIG. 8 shows a flowchart of a method according to the present invention for optical imaging.

In a first step (S1) 801, said optical probe is provided, and a radiation source is provided (S2) 802 which is optically coupled to the optical probe. As discussed previously in FIG. 2, the probe is arranged for guiding radiation emitted from the radiation source to a region of interest. In a third step (S3) 803, an imaging process is performed with an imaging detector optically coupled to the optical probe, the detector being arranged for imaging using reflected radiation from the region of interest.

For further details, see the discussion under FIGS. 2 and 3.

Certain specific details of the disclosed embodiment are set forth for purposes of explanation rather than limitation, so as to provide a clear and thorough understanding of the present invention. However, it should be understood by those skilled in this art, that the present invention might be practiced in other embodiments that do not conform exactly to the details set forth herein, without departing significantly from the spirit and scope of this disclosure. Further, in this context, and for the purposes of brevity and clarity, detailed descriptions of well-known apparatuses, circuits and methodologies have been omitted so as to avoid unnecessary detail and possible confusion.

Reference signs are included in the claims, however the inclusion of the reference signs is only for clarity reasons and should not be construed as limiting the scope of the claims.

The invention claimed is:

1. An optical probe, comprising:
   an optical guide having a proximal end and a distal end;
   an actuation means comprising at least one driving coil and a magnet either of which being attached to the optical guide, wherein by supplying a driving current through the at least one driving coil a magnetic flux is generated which interacts with the magnet and forms a driving force acting on the optical guide causing a displacement of the distal end of the optical guide;
   a position measuring system comprising:
      a position measuring coil configured to monitor a position of the optical guide, an internal arrangement of the position measuring coil and the at least one driving coil being such that said displacement of the distal end of the optical guide causes a change in the internal arrangement;
      a power supply configured to supply an additional sensing current through the at least one driving coil, the additional sensing current causing an induced voltage in the position measuring coil and thus generates a magnetic coupling between the position measuring coil and the at least one driving coil; and
      a position measuring device configured to measure the displacement of the distal end of the optical guide by measuring the induced voltage resulting from the change in said internal arrangement due to the additional sensing current, the induced voltage being indicative for the position of the distal end,
   wherein the at least one driving coil comprises X-driving coils and Z-driving coils for displacing the distal end of the optical guide along different axes,
   wherein the additional sensing current comprises a high frequency alternating current (AC) through the X-driving coils,
   wherein the additional sensing current further comprises a further high frequency alternating current (AC) through the Z-driving coils, and
   wherein the high frequency of the AC through the X-driving coils has a frequency which is different from a frequency of the further high frequency AC through the Z-driving coils.

2. The optical probe according to claim 1, wherein the high frequency alternating current (AC) has a frequency higher than a frequency of the driving current, the high frequency of the AC being selected such that its contribution to the displacement of the optical guide is minimized.

3. The optical probe according to claim 1, wherein the X-driving coils are arranged opposite to each other along an x-axis with the optical guide there between such that a longitudinal axis of the X-driving coils is perpendicular to the longitudinal axis of the optical guide, the driving current supplied through the X-driving coils causing displacement of the distal end of the optical guide along the x-axis, the high frequency of the AC being higher than a frequency of the driving current.

4. The optical probe according to claim 3, wherein the Z-driving coils are arranged opposite to each other along a z-axis with the optical guide there between such that a longitudinal axis of the Z-driving coils is perpendicular to the longitudinal axis of the optical guide, the driving current supplied through the Z-driving coils causing displacement of the distal end of the optical guide along the z-axis perpendicular to the x-axis, the further high frequency of the AC being higher than the frequency of the driving current.

5. The optical probe according to claim 2, wherein a frequency of the high frequency AC is in the range of 100 kHz-1 MHz.

6. The optical probe according to claim 1, further comprising a lens system rigidly coupled to the distal end of the optical guide.

7. The optical probe according to claim 1, further comprising a housing with a cavity for the optical guide, the housing having at its distal end a transparent window.

8. The optical probe according to claim 1, wherein the at least one driving coil is mounted to the housing and the position measuring coil is mounted to the optical guide.

9. An optical imaging system comprising:
   an optical probe;
   a radiation source optically coupled to the optical probe, the probe being arranged for guiding radiation emitted from the radiation source to a region of interest; and
   an imaging detector optically coupled to the optical probe, the detector being arranged for imaging using reflected radiation from the region of interest,
   wherein the optical probe comprises:
   an optical guide having a proximal end and a distal end;
   an actuation means comprising at least one driving coil and a magnet either of which being attached to the optical guide, wherein by supplying a driving current through the at least one driving coil a magnetic flux is generated which interacts with the magnet and forms a driving force acting on the optical guide causing a displacement of the distal end of the optical guide; and
   a position measuring system comprising:
      a position measuring coil configured to monitor a position of the optical guide, an internal arrangement of the position measuring coil and the at least one driving coil being such that said displacement of the distal end of the optical guide causes a change in the internal arrangement;
      a power supply configured to supply an additional sensing current through the at least one driving coil, the additional sensing current causing an induced voltage in the position measuring coil and thus generates a magnetic coupling between the position measuring coil and the at least one driving coil; and a position measuring device configured to measure the displacement of the distal end of the optical guide by measuring the induced voltage resulting from the change in said internal arrangement due to the additional sensing current, the induced voltage being indicative for the position of the distal end, wherein the at least one driving coil comprises X-driving coils and Z-driving coils for displacing the distal end of the optical guide along different axes, wherein the additional sensing current comprises a high frequency alternating current (AC) through the X-driving coils, wherein the additional sensing current further comprises a further high frequency alternating current (AC) through the Z-driving coils, and wherein the high frequency of the AC through the X-driving coils has a frequency which is different from a frequency of the further high frequency AC through the Z-driving coils.

10. The optical imaging system according to claim 9, wherein the frequency of the additional sensing current is in the range of 100 kHz-1 MHz.

11. The optical imaging system according to claim 9, wherein the frequency of the driving current is up to 1 kHz.

12. A method for optical imaging, the method comprising the acts of:

providing an optical probe;

providing a radiation source which is optically coupled to the optical probe, the probe being arranged for guiding radiation emitted from the radiation source to a region of interest; and performing an imaging process with an imaging detector optically coupled to the optical probe, the detector being arranged for imaging using reflected radiation from the region of interest, wherein the optical probe comprises:

an optical guide having a proximal end and a distal end;

an actuation means comprising at least one driving coil and a magnet either of which being attached to the optical guide, wherein by supplying a driving current through the at least one driving coil a magnetic flux is generated which interacts with the magnet and forms a driving force acting on the optical guide causing a displacement of the distal end of the optical guide; and a position measuring system comprising:

a position measuring coil configured to monitor a position of the optical guide, an internal arrangement of the position measuring coil and the at least one driving coil being such that said displacement of the distal end of the optical guide causes a change in the internal arrangement;

a power supply configured to supply an additional sensing current through the at least one driving coil, the additional sensing current causing an induced voltage in the position measuring coil and thus generates a magnetic coupling between the position measuring coil and the at least one driving coil; and a position measuring device configured to measure the displacement of the distal end of the optical guide by measuring the induced voltage resulting from the change in said internal arrangement due to the additional sensing current, the induced voltage being indicative for the position of the distal end, wherein the at least one driving coil comprises X-driving coils and Z-driving coils for displacing the distal end of the optical guide along different axes, wherein the additional sensing current comprises a high frequency alternating current (AC) through the X-driving coils, wherein the additional sensing current further comprises a further high frequency alternating current (AC) through the Z-driving coils, and wherein the high frequency of the AC through the X-driving coils has a frequency which is different from a frequency of the further high frequency AC through the Z-driving coils.

13. The optical probe of claim 1, wherein the position measuring coil is mounted around the optical guide such that a longitudinal axis of the position measuring coil is substantially parallel to a longitudinal axis of the optical guide.

14. The optical imaging system of claim 9, wherein the position measuring coil is mounted around the optical guide such that a longitudinal axis of the position measuring coil is substantially parallel to a longitudinal axis of the optical guide.

15. The method of claim 12, wherein the position measuring coil is mounted around the optical guide such that a longitudinal axis of the position measuring coil is substantially parallel to a longitudinal axis of the optical guide.

* * * * *